(12) United States Patent
Zülli et al.

(10) Patent No.: US 7,431,940 B2
(45) Date of Patent: Oct. 7, 2008

(54) METHODS FOR TREATMENT OF HUMAN SKIN DAMAGED BY LASER TREATMENT OR CHEMICAL PEELINGS AND COMPOSITIONS USEFUL IN SUCH METHODS

(75) Inventors: Fred Zülli, Küttingen (CH); Margrit Neuenschwander, Rombach (CH); Nicola Cardozo-Hofmann, Unterkulm (CH)

(73) Assignee: Mibelle AG Cosmetics, Buchs (CH)

( * ) Notice: Subject to any disclaimer, the term of this patent is extended or adjusted under 35 U.S.C. 154(b) by 936 days.

(21) Appl. No.: 10/992,169

(22) Filed: Nov. 18, 2004

(65) Prior Publication Data
US 2005/0100592 A1 May 12, 2005

Related U.S. Application Data

(62) Division of application No. 10/179,103, filed on Jun. 25, 2002, now Pat. No. 6,986,903.

(30) Foreign Application Priority Data
Jul. 13, 2001 (CH) .................................... 1296/01

(51) Int. Cl.
| | |
|---|---|
| A61K 9/127 | (2006.01) |
| A61K 8/02 | (2006.01) |
| A61K 9/00 | (2006.01) |
| A61K 31/70 | (2006.01) |
| A61K 31/715 | (2006.01) |
| A61K 31/12 | (2006.01) |

(52) U.S. Cl. .................. 424/450; 424/400; 424/401; 514/23; 514/54; 514/690

(58) Field of Classification Search ................ 424/405, 424/400, 401; 514/23, 54, 690
See application file for complete search history.

(56) References Cited

U.S. PATENT DOCUMENTS

| 4,454,159 A | 6/1984 | Musher |
| 5,738,856 A | 4/1998 | Korb et al. |
| 5,851,543 A | 12/1998 | Korb et al. |
| 6,342,486 B1 * | 1/2002 | Zulli et al. ............... 514/54 |
| 6,506,391 B1 * | 1/2003 | Biatry .................... 424/401 |

FOREIGN PATENT DOCUMENTS

| FR | 2794366 | | 9/1999 |
| JP | 58180410 A | * | 10/1983 |
| WO | WO 97/16166 | | 5/1997 |
| WO | WO 98/55082 | | 12/1998 |

OTHER PUBLICATIONS

Drosner, Michael, *Aktuelle Techniken des Laser Skin-Resurfacing*, Kosmetische Medizin, Supplement Jan. 2001, pp. 8-10.

* cited by examiner

*Primary Examiner*—Shengjun Wang
(74) *Attorney, Agent, or Firm*—Maginot, Moore & Beck

(57) ABSTRACT

Methods for treatment of human skin damaged by laser treatment or chemical peelings comprise the topical application of an effective amount of a lamellar oil-in-water system. In accordance with the methods, the lamellar oil-in-water system comprises at least one vegetable oil as the oily component, a hydrogenated phospholipid as emulsifier comprising not more than 10 percent by weight of negatively charged phospholipids with the remainder being neutral phospholipids, and sodium carboxymethyl β-glucan (Sodium Carboxymethyl Betaglucan) as a compound for improving wound healing. The lamellar oil-in-water system used in the method may further comprise coenzyme Q10 as a compound for improving skin regeneration.

4 Claims, 1 Drawing Sheet

Fig. 1: Transepidermal Water Loss (TEWL)
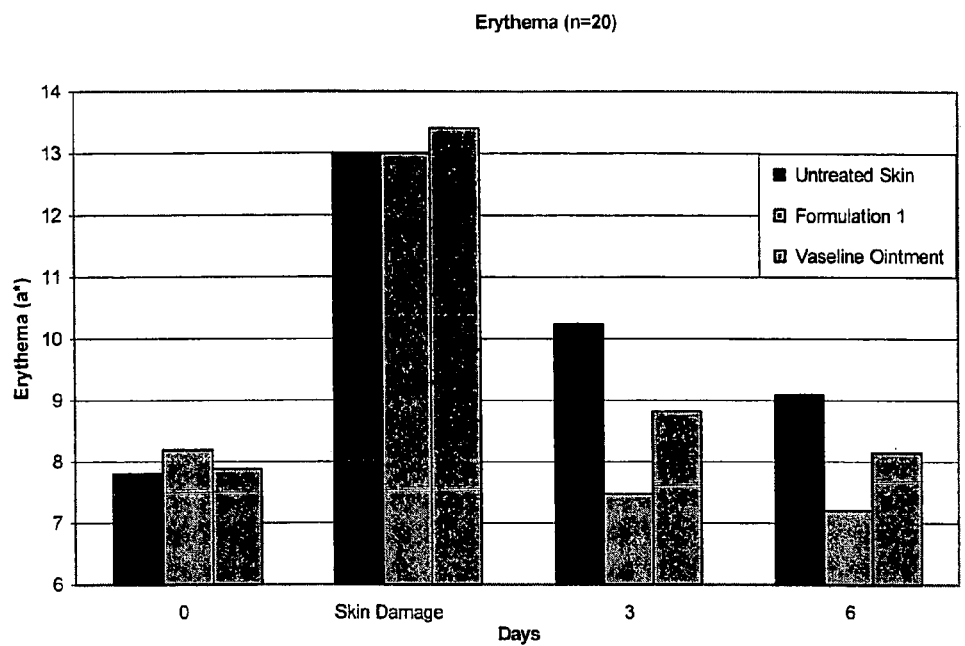
Fig. 2: Erythema
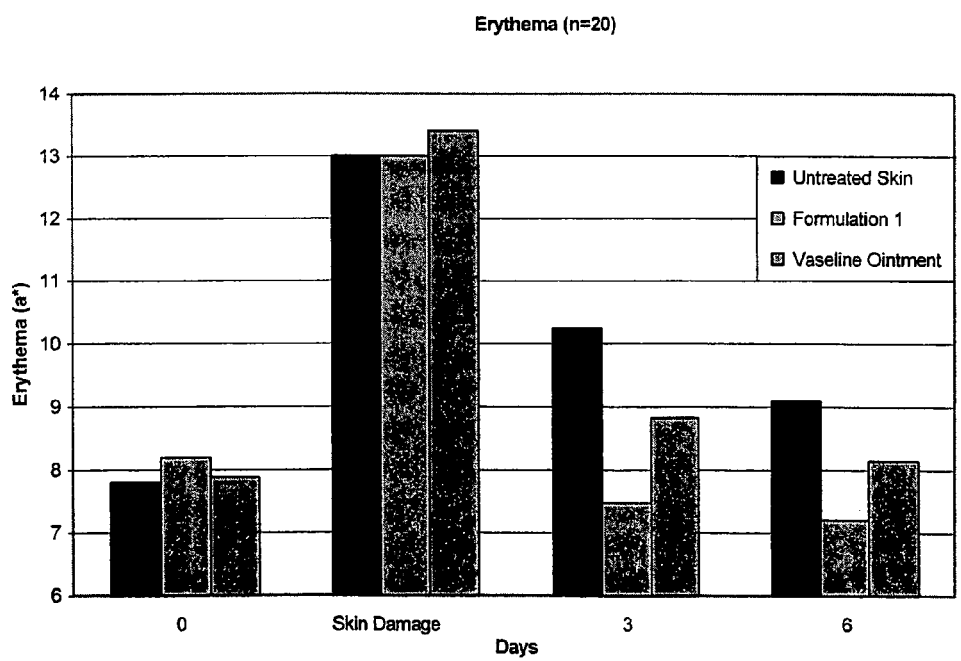

METHODS FOR TREATMENT OF HUMAN SKIN DAMAGED BY LASER TREATMENT OR CHEMICAL PEELINGS AND COMPOSITIONS USEFUL IN SUCH METHODS

CROSS-REFERENCE TO RELATED APPLICATIONS

This application is a divisional application of U.S. Ser. No. 10/179,103, now U.S. Pat. No. 6,986,903, filed Jun. 25, 2002, which claims priority of Switzerland 1296/01, filed Jul. 13, 2001.

FIELD OF THE INVENTION

The present invention is concerned with methods for treatment of human skin damaged by laser treatment or chemical peelings and compositions useful in carrying out such methods.

BACKGROUND OF THE INVENTION

Laser treatments are nowadays widely used in cosmetics, dermatology and surgery. A wide selection of laser devices are available for these purposes, such as:

Neodymium Yttrium-Aluminium-Garnet Laser [Neodymium:YAG] (1064 nm)
    This laser provides a high penetration depth and produces a photothermolysis. By superposition of a potassium titanyl phosphate crystal the frequency can be doubled, thus halving the wave length to 532 nm. The emerging green light is well absorbed by structures containing melanine or oxyhemoglobin. Thus, this laser is used for the treatment of epidermic pigmented lesions.

Ruby Laser (694 nm)
    The red light of the ruby laser, which is very well absorbed by melanin and dark colored particles, is suitable for the treatment of Lentigo benigna (café au lait spot) for its short exposure time (25 to 40 ns) by which the thermic lesion of the surrounding tissues is minimized.

Alexandrite Laser (755 nm)
    This laser is suitable for the treatment of dark tattoos.

$CO_2$-Laser (10'600 nm)
    The light of this laser is absorbed by the tissue fluid which results in coagulation and vaporization of the tissue. In its continuous wave mode this laser can be used as a light scalpel. However, in its pulsed mode this laser is well suitable for "Skin Resurfacing". Thereby, the uppermost dermal layers (Stratum corneum and epidermis) can purposefully and extensively be removed. A total ablation of the face is often made for producing a visible rejuvenation. By a selective photothermolysis the removal of the skin happens faster than the generation of heat. Besides the removal of the epidermis, the residual heat provokes a firming of the connective tissue as well a new synthesis of collagen. The regrowing skin is free from wrinkles and scars.

Erbium Yttrium Aluminium Granat Laser [Erbium:YAG] (2940 nm)
    This pulsed laser has an indication spectrum which is similar to that of the $CO_2$-laser. However, the thermic tissue effect is lower. Thus, the painfulness and the risk of scars formation is reduced. However, this advantage is partially neutralized by the fact that the operation method is bloody. By the use of this laser skin layers of a thickness of 5 to 15 µm can purposefully be removed. Thus, this laser is also particularly useful for cosmetic treatments.

The possibilities of laser treatment are very wide and are permanently improved. A synopsis is given in the publication Michael Drosner, Kosmetologika 2001, Supplement 1/2001, pages 8 to 10.

In chemical peelings the uppermost skin layer is removed as well, this time by aggressive chemicals. Thereafter, the regrowing skin is rejuvenated. This becomes apparent by a reduction of wrinkles and of the roughness of the skin. For such chemical peelings, substances such as phenol, trichloroacetic acid, α- and β-hydroxyacids (glycolic acid, lactic acid, salicylic acid) are used in various concentrations. After treatment of the skin with these substances in various concentrations for several days the skin is irritated and shows an increased transepidermal water loss.

All laser treatments and chemical treatments of the skin produce slight or severe wounds which are to be treated with cosmetic or pharmaceutical products to enable the skin to resume its normal function. Besides the cooling effect of an aftercare, there is a need for occlusive measure in order to reduce the transepidermal water loss and to protect the open skin against environmental influences, such as micro-organisms, dirt, viruses, or chemicals. Immediately after the laser treatment a protection by a foil or a vulnerary gel is often applied. However, creams or ointments are used for an extensive aftercare.

At present quite a number of products for the post-treatment of skin damaged by laser treatments and chemical peelings are on sale and used. Most of these products are based on a vaseline formulation, such as e.g. "Aquaphor®" of Beiersdorf AG, Germany, and "Catrix 10®" of Lescarden Inc., USA. These products are very simple, relatively reasonable in price, and they produce a good occlusion. A further advantage of these products is that they contain no or only very little water, and thus need not to be preserved.

However, an important disadvantage of these products is that they comprise a fatty component on the basis of mineral oils, and thus are not optimal for skin regeneration. Furthermore, these formulations are unsuitable for the incorporation of aqueous active components having wound healing properties, such as e.g. dexpanthenol. A further disadvantage is that they produce an unpleasant greasy skin-feeling.

A better skin-feeling and a more pleasant application can be reached by using creams. Therefore, such oil-in-water or water-in-oil formulations are used for post-laser treatments and after chemical peelings, such as e.g. "Post-Laser Treatment Kit®" of Skin Medica, USA, and "Nutritive Moisturizing Calendula Cream®" of TT Cosmetica Activa, Spain. Such emulsions allow a wider scope in using active components which promote wound healing and regeneration of the skin. However, very often such products contain compounds which provoke irritations and allergic manifestations, such as e.g. preservatives, perfumes, or plant extracts. However, a most important disadvantage of such formulations is the presence of water-in-oil and oil-in-water emulsifiers. These compounds negatively influence the skin regeneration. Moreover, they also emulsify the skin lipids, by which the formation of a barrier function is deteriorated.

As said above, laser treatments and chemical peeling produce very similar surface effects, inasmuch as they remove the uppermost dermal layers, i.e. Stratum corneum and epidermis. The skin then no longer comprises any corneocytes.

The publication WO 97/16166, corresponding to U.S. Pat. Nos. 5,738,543 and 5,851,543, describes methods for treatment of human skin by enhancing formation of lamellae between corneocytes within the skin by topical application of a bilayer component that is a mixture of a negatively charged phospholipid and a triglyceride. The compositions to be applied also comprise mineral oils. Such treatments are completely different from the post-treatment of skin damaged by laser treatments or chemical peelings, because—as said above—the damaged skin does no longer comprise any corneocytes.

The publication WO 98/55082 describes a dermatological healing kit which comprises a pigment stabilizer and anti-inflammatory emollient, and which is said to be useful for post-treating skin after laser treatments. The purpose of using this kit is to avoid darkening of the laser treated skin and to relieve skin inflammations. However, this kit is unsuitable for rebuilding the uppermost dermal layers, i.e. Stratum corneum and epidermis, of skin damaged by laser treatment or chemical peelings.

U.S. Pat. No. 4,454,159 describes a dermatological composition comprising a special combination of lipids/lipoids which is said to soothe and condition irritated, pruritic and dry skin. However, this composition too is unsuitable for rebuilding the uppermost dermal layers, i.e. Stratum corneum and epidermis, of skin damaged by laser treatment or chemical peelings.

Finally, the publication FR 2,794,366 describes a dermatological composition comprising a ceramide, cholesterol, fatty acids, a triglyceride, lecithin, and phytosphingosine. This composition is said to be useful in treating skin damaged by cuts, burns, inflammations or acne. However once again, this composition is unsuitable for rebuilding the uppermost dermal layers, i.e. Stratum corneum and epidermis, of skin damaged by laser treatment or chemical peelings.

OBJECTS OF THE INVENTION

A first object of the present invention is to eliminate the disadvantage of the prior art in the treatment of human skin damaged by laser treatment or chemical peelings.

Another object of the present invention is to provide methods and compositions useful in such methods for a highly effective treatment of human skin damaged by laser treatments or chemical peelings.

The afore-mentioned and further objects, advantages and features will be apparent form the following specification.

SUMMARY OF THE INVENTION

To meet these and other objects, the invention provides methods for treatment of human skin damaged by laser treatment or chemical peelings, said methods comprising topical application of a lamellar oil-in-water system, said lamellar oil-in-water system comprising at least one vegetable oil as the oily component and at least one hydrogenated phospholipid as emulsifier, said at least one hydrogenated phospholipid comprising not more than 10 percent by weight of negatively charged phospholipids the remainder being neutral phospholipids.

The invention also provides compositions useful in carrying said methods, said compositions being lamellar oil-in-water systems comprising at least one vegetable oil as the oily component and at least one hydrogenated phospholipid as emulsifier, said at least one hydrogenated phospholipid comprising not more than 10 percent by weight of negatively charged phospholipids the remainder being neutral phospholipids.

Said lamellar oil-in-water systems may further comprise sodium carboxymethyl β-glucan (Sodium Carboxymethyl Betaglucan) as a compound for improving wound healing and/or coenzyme Q10 as a compound for improving skin regeneration.

Said oil-in water structures mimic the natural skin barrier until the epidermis and the Stratum corneum become regenerated. They also positively influence and accelerate the wound healing.

The lamellar oil-in-water systems comprising hydrogenated phospholipids as emulsifier can be produced by high pressure homogenization, e.g. by means of homogenizers such as a Gaulin® or a Microfluidizer® at 100 to 1800 bar ($10^7$ to $1.8 \cdot 10^8$ Pa), without the need of strongly heating either the aqueous phase or the oily phase. In particular, said lamellar oil-in-water systems can be prepared by first homogenizing a concentrate comprising the emulsifier and at least part of the oily component, and thereafter admixing the remainder of the components without further homogenization. The oil-in-water systems prepared this way are well-tolerated by the skin and provoke a lasting humidification of the skin.

The lamellar oil-in-water basic formulation is very suitable for the integration of further active compounds which promote regeneration of the skin an/or reduce skin irritations which normally appear after such drastic treatments.

One of such active compound is e.g. sodium carboxymethyl β-glucan (Sodium Carboxymethyl Betaglucan), a substance which protects the skin against irritations and allergens (cf. D. Castelli, L. Colin, E. Camel und G. Ries, Contact Dermatitis 1998, No. 38, pages 123 to 126) and promotes wound healing. It is produced from bakers yeast and is a water soluble active compound which surprisingly is very suitable for optimizing oil-in-water formulations for use in post laser treatments.

Coenzym Q10 is a further substance which is excellently suitable for use in lamellar formulations. Coenzym Q10 is an endogenous substance which promotes generating of energy in the cell mitochondria, and which also acts as antioxidant. The bioavailability of Coenzym Q10 in the lamellar oil-in-water formulations can be improved by encapsulating it in nanoemulsions of <200 nm (cf. F. Zülli und F. Suter, SÖFW-Journal 123, No. 13/97, page 880).

Many oily components can provoke skin incompatibility. This danger is even increased after laser treatments and chemical peelings. In the lamellar oil-in-water formulations according to the present invention a vegetable oil is used as oily component, preferably a glycerol trioleate. This compound has an excellent compatibility and promotes regeneration of the skin.

The following examples and formulations will explain preferred embodiments of the present invention more in detail.

All numerals given below are percents by weight. The indication of the ingredients is made according to the INCI (International Nomenclature of Cosmetics Ingredients) nomenclature.

EXAMPLES

Formulation 1: Skin Care Product for Use After Laser Treatments

| | |
|---|---|
| Vegetable Oil | 13.00% |
| Butyrospermum Parkii | 10.00% |
| Pentylene Glycol | 6.80% |

-continued

| | |
|---|---|
| Squalane | 2.50% |
| Hydrogenated Lecithin | 2.30% |
| Glycerin | 1.00% |
| Palm Glycerides | 1.00% |
| Alcohol | 0.80% |
| Tocopheryl Acetate | 0.30% |
| Propylene Glycol | 0.30% |
| Caprylic/Capric Triglyceride | 0.20% |
| Sodium Carboxymethyl Betaglucan | 0.10% |
| Ubiquinone | 0.08% |
| Acrylates/C10-30 Alkyl Acrylate Crosspolymer | 0.10% |
| Xanthan Gum | 0.05% |
| Lecithin | 0.04% |
| Sodium Hydroxide | 0.01% |
| Ceramide 3 | 0.04% |
| Aqua | ad 100% |

Formulation 2: Skin Care Product for Use After Chemical Peelings

| | |
|---|---|
| Vegetable Oil | 13.50% |
| Decyl Oleate | 10.00% |
| Pentylene Glycol | 6.25% |
| Glycerin | 2.00% |
| Aloe Barbadensis | 5.75% |
| Hydrogenated Lecithin | 1.63% |
| Butyrospermum Parkii | 0.75% |
| Squalane | 0.25% |
| Alcohol | 0.20% |
| Xanthan Gum | 0.20% |
| Propylene Glycol | 0.10% |
| Carbomer | 0.04% |
| Sodium Carboxymethyl Betaglucan | 0.03% |
| Sodium Hydroxide | 0.03% |
| Ceramide 3 | 0.03% |
| Aqua | ad 100% |

Formulation 3: Day Cream

| | |
|---|---|
| Caprylic/Capric Triglyceride | 10.00% |
| Vegetable Oil | 2.82% |
| Butyrospermum Parkii | 5.00% |
| Pentylene Glycol | 6.80% |
| Glycerin | 3.00% |
| Glucose | 2.00% |
| Hydrogenated Lecithin | 6.50% |
| Squalane | 7.00% |
| Tocopheryl Acetate | 0.30% |
| Ceramide 3 | 0.01% |
| Aqua | ad 100% |

Formulation 4: Moisture Protection Cream (i)

| | |
|---|---|
| Caprylic/Capric Triglyceride | 28.96% |
| Pentylene Glycol | 5.00% |
| Hydrogenated Lecithin | 3.96% |
| Butyrospermum Parkii | 1.98% |
| Glycerin | 1.98% |
| Squalane | 0.66% |
| Ceramide 3 | 0.01% |
| Aqua | ad 100% |

Formulation 5: Moisture Protection Cream (ii)

| | |
|---|---|
| Caprylic/Capric Triglyceride | 16.89% |
| Pentylene Glycol | 5.00% |
| Propylene Glycol | 2.50% |
| Hydrogenated Lecithin | 1.98% |
| Butyrospermum Parkii | 1.00% |
| Glycerin | 1.00% |
| Squalane | 0.33% |
| Xanthan Gum | 0.15% |
| Carbomer | 0.10% |
| Sodium Hydroxide | 0.06% |
| Ceramide 3 | 0.004% |
| Aqua | ad 100% |

Composition of Vaseline Ointment (Aquaphor®)
Mineral oil
Ceresin
Lanolin Alcohol
Panthenol
Glycerin
Bisabolol Efficiency Tests The efficiency of formulation according to the present invention is demonstrated by the following tests. Thereby reference is made to the graphics enclosed herewith as drawings.

1. Skin Protection Test with 20 Test Persons

The upper skin layers of the test persons at their forearms were removed by tearing them off 20 times each with cellofilm, thus simulating a chemical peeling or a laser treatment. These damages of the skin provoked a heavy increase of the transepidermal water loss. Thereafter, the skin areas were treated twice a day with various formulations, and skin regeneration was followed during the following days by measuring the Transepidermal Water Loss and measuring the erythema. The first measurement was made before the damage of the skin, the second one 4 hours after said damage, and further measurement were made on the 3rd and 6th day, each 4 hours after the last application of the products.

Results: Transepidermal Water Lloss (TEWL)

FIG. 1 shows that the Transepidermal Water Loss on the 3rd and 6th day after treatment with the above described Formulation 1 was distinctly reduced as compared with untreated skin or skin treated with Vaseline Ointment (Aquaphor®)). The lamellar oil-in-water structures of Formulation 1 mimic the skin barrier and thus protect the skin against desiccation. The TEWL values were determined by means of a Tewameter® TM 210 of Courage+Khazaka GmbH, Cologne, Germany.

Results: Erythema

FIG. 2 shows that erythema and skin irritation on the 3rd and 6th day after treatment with the above described Formulation 1 was distinctly reduced as compared with untreated skin or skin treated with vaseline ointment (Aquaphor®). The lamellar oil-in-water structures of Formulation 1 are well-tolerated and allow a quick regeneration of the skin. Sodium Carboxymethyl Betaglucan protect against irritation and allergic manifestations. The erythema was determined by means of a Chromameter® CR 300 of Minolta, Japan.

2. Regeneration of the Skin After Laser Treatments

33 Test persons underwent a laser treatment by a dermatologist, 6 of them a total "facial resurfacing", 15 a partial "facial resurfacing", and 12 a local treatment. The lamellar oil-in-water Formulation 1 was used as a post laser treatment. The patients used the cream 4 to 6 times a day by themselves for 2 to 4 weeks.

Results

In his opinion, the dermatologist's states as follows:

Very good compatibility of the formulation (no incompatibilities).

Acceleration of the total regeneration process.

Acceleration of the epithelization by Formulation 1 (about 2 days quicker than with conventional Vaseline Ointments)

He is recommending the use of the lamellar oil-in-water formulation according to the invention for skin care after laser treatments.

3. Skin Care with Lamellar Day Creams

Formulations 4 and 5 and an ordinary moisture cream were tested on 20 test persons. The products were applied twice a day on the forearm for 30 days. Thereafter, the application was stopped, and the moistness of the skin was determined. Were a ordinary moisture cream had been applied, the humidity of the skin decreased again already on the first day after the post treatment. Contrary to this, the skin areas which had been treated with Formulations 4 and 5 showed a skin moistness which was 80% and 120%, respectively, higher than those treated with an ordinary moisture cream.

What is claimed is:

1. A method for treatment of human skin damaged by laser treatment, said method comprising topical application of an effective amount of a lamellar oil-in-water, said lamellar oil-in-water system comprising:

at least one vegetable oil as the oily component;

a hydrogenated phospholipid as emulsifier, said hydrogenated phospholipid comprising not more than 10 percent by weight of negatively charged phospholipids, the remainder being neutral phospholipids; and sodium carboxymethyl β-glucan (Sodium Carboxymethyl Betaglucan) as a compound for improving wound healing.

2. The method of claim 1 wherein said lamellar oil-in-water system further comprises coenzyme Q10 as a compound for improving skin regeneration.

3. A method for treatment of human skin damaged by chemical peelings, said method comprising topical application of an effective amount of a lamellar oil-in-water, said lamellar oil-in-water system comprising:

at least one vegetable oil as the oily component;

a hydrogenated phospholipid as emulsifier, said hydrogenated phospholipid comprising not more than 10 percent by weight of negatively charged phospholipids, the remainder being neutral phospholipids; and sodium carboxymethyl β-glucan (Sodium Carboxymethyl Betaglucan) as a compound for improving wound healing.

4. The method of claim 3 wherein said lamellar oil-in-water system further comprises coenzyme Q10 as a compound for improving skin regeneration.

* * * * *